(12) United States Patent
Negi et al.

(10) Patent No.: US 10,117,005 B2
(45) Date of Patent: Oct. 30, 2018

(54) SYSTEM AND METHOD FOR DEVICE ACTION AND CONFIGURATION BASED ON USER CONTEXT DETECTION FROM SENSORS IN PERIPHERAL DEVICES

(71) Applicant: Intel Corporation, Santa Clara, CA (US)

(72) Inventors: Indira Negi, San Jose, CA (US); Lakshman Krishnamurthy, Portland, OR (US); Fuad Al-Amin, Sunnyvale, CA (US); Xiaochao Yang, San Jose, CA (US); Brian K. Vogel, Santa Clara, CA (US); Jun Li, Pleasanton, CA (US); Alexander Essaian, San Jose, CA (US); Sai Hemachandra Vemprala, Santa Clara, CA (US); Donnie H. Kim, Santa Clara, CA (US); Lama Nachman, San Francisco, CA (US); Haibin Liu, Santa Clara, CA (US)

(73) Assignee: INTEL CORPORATION, Santa Clara, CA (US)

( * ) Notice: Subject to any disclaimer, the term of this patent is extended or adjusted under 35 U.S.C. 154(b) by 0 days.

(21) Appl. No.: 15/807,246

(22) Filed: Nov. 8, 2017

(65) Prior Publication Data
US 2018/0070155 A1 Mar. 8, 2018

Related U.S. Application Data

(63) Continuation of application No. 14/365,653, filed as application No. PCT/US2013/078144 on Dec. 28, 2013.

(51) Int. Cl.
G08C 19/22 (2006.01)
H04Q 9/00 (2006.01)
(Continued)

(52) U.S. Cl.
CPC .............. *H04Q 9/00* (2013.01); *A61B 5/0022* (2013.01); *A61B 5/01* (2013.01); *A61B 5/024* (2013.01);
(Continued)

(58) Field of Classification Search
CPC ............................ A61B 5/02438; F24F 11/64
(Continued)

(56) References Cited

U.S. PATENT DOCUMENTS

2003/0233051 A1 12/2003 Verjus et al.
2005/0059870 A1 3/2005 Aceti
(Continued)

FOREIGN PATENT DOCUMENTS

KR 100869245 11/2008
KR 20100036305 4/2010
(Continued)

OTHER PUBLICATIONS

European Patent Office, "Communication pursuant to Article 94(3) EPC," issued in connection with European Patent Application No. 13 900 501.1, dated Mar. 7, 2018, 6 pages.
(Continued)

*Primary Examiner* — Fabricio R Murillo Garcia
(74) *Attorney, Agent, or Firm* — Hanley, Flight & Zimmerman, LLC

(57) ABSTRACT

A system and method for device action and configuration based on user context detection from sensors in peripheral devices are disclosed. A mobile device includes an interface to receive sensor data from a sensor of a wearable peripheral device worn by a user. The mobile device further includes at least one processor to: identify an activity engaged in by the user based on the sensor data, detect a completion of the activity based on the sensor data, and configure the mobile
(Continued)

device to generate a notification to the user in response to the detection of the completion of the activity.

9 Claims, 9 Drawing Sheets

(51) Int. Cl.
| | |
|---|---|
| A61B 5/01 | (2006.01) |
| A61B 5/024 | (2006.01) |
| A61B 5/053 | (2006.01) |
| G10L 19/00 | (2013.01) |
| H04M 1/725 | (2006.01) |
| H04W 68/00 | (2009.01) |
| H04R 1/10 | (2006.01) |
| A61B 5/00 | (2006.01) |
| H04W 88/02 | (2009.01) |
| H04M 1/60 | (2006.01) |

(52) U.S. Cl.
CPC ............ *A61B 5/0533* (2013.01); *G10L 19/00* (2013.01); *H04M 1/7253* (2013.01); *H04M 1/72569* (2013.01); *H04R 1/1091* (2013.01); *H04W 68/00* (2013.01); *H04M 1/6058* (2013.01); *H04M 1/6066* (2013.01); *H04Q 2209/40* (2013.01); *H04R 2201/107* (2013.01); *H04R 2499/11* (2013.01); *H04W 88/02* (2013.01)

(58) Field of Classification Search
USPC .................................................. 340/870.07
See application file for complete search history.

(56) References Cited

U.S. PATENT DOCUMENTS

| | | | |
|---|---|---|---|
| 2006/0149905 | A1 | 7/2006 | Park et al. |
| 2008/0146890 | A1 | 6/2008 | LeBoeuf et al. |
| 2009/0097683 | A1* | 4/2009 | Burns ................ H04R 25/02 381/324 |
| 2010/0248784 | A1 | 9/2010 | Stolarz et al. |
| 2011/0082711 | A1 | 4/2011 | Poeze et al. |
| 2011/0148922 | A1 | 6/2011 | Son et al. |
| 2012/0329529 | A1 | 12/2012 | van der Raadt |
| 2014/0347265 | A1* | 11/2014 | Aimone ................ G09G 3/003 345/156 |
| 2015/0072672 | A1 | 3/2015 | Jacobsen et al. |
| 2018/0055450 | A1* | 3/2018 | LeBoeuf ............. G06F 19/3406 |

FOREIGN PATENT DOCUMENTS

| | | |
|---|---|---|
| WO | 2007052886 | 5/2007 |
| WO | 2015099796 | 7/2015 |

OTHER PUBLICATIONS

European Patent Office, "Extended European Search Report," issued in connection with European Patent Application No. 13900501.1, dated Jul. 28, 2017, 8 pages.

European Patent Office, "Communication pursuant to Rules 70(2) and 70a(2) EPC," issued in connection with European Patent Application No. 13900501.1, dated Aug. 16, 2017, 1 page.

Korean Intellectual Property Office, "Office Action," issued in connection with Korean Patent Application No. 10-2016-7014085, dated Jul. 25, 2017, 7 pages.

International Searching Authority, "International Search Report and Written Opinion," issued in connection with International Patent Application No. PCT/US2013/078144, dated Sep. 22, 2014, 7 pages.

International Bureau, "International Preliminary Report on Patentability," issued in connection with International Patent Application No. PCT/US2013/078144, dated Jun. 28, 2016, 5 pages.

United States Patent and Trademark Office, "Final Office Action," issued in connection with U.S. Appl. No. 14/365,653, dated Aug. 8, 2017, 30 pages.

United States Patent and Trademark Office, "Non-Final Office Action," issued in connection with U.S. Appl. No. 14/365,653, dated Feb. 8, 2017, 21 pages.

* cited by examiner

SYSTEM AND METHOD FOR DEVICE ACTION AND CONFIGURATION BASED ON USER CONTEXT DETECTION FROM SENSORS IN PERIPHERAL DEVICES

RELATED APPLICATIONS

This patent arises from a continuation of U.S. patent application Ser. No. 14/365,653 filed on Jan. 29, 2016, which is a National Stage Entry of International Patent Application Serial No. PCT/US2013/078144 filed on Dec. 28, 2013. Each of the above-referenced patent applications is hereby incorporated herein by reference in its entirety.

TECHNICAL FIELD

This patent application relates to electronic systems, peripheral devices, mobile devices, and computer-implemented software, according to various example embodiments, and more specifically to a system and method for device action and configuration based on user context detection from sensors in peripheral devices.

BACKGROUND

Smartphones are becoming the predominant link between people and information. Most current smartphones or other mobile devices provide a capability to use mobile software applications (apps). A mobile software application (app) can embody a defined set of functionality and can be installed and executed on a mobile device, such as a smartphone, a tablet device, laptop computer, a digital camera, or other form of mobile computing, imaging, or communications device. Conventional mobile apps are available that focus on particular applications or functionality sets. Additionally, most standard mobile phones and other mobile devices have an audio/microphone connector or audio jack into which a headset, earbuds, or other peripheral device connector can be plugged. Most standard headsets or earbud accessories also include a microphone so the user can both hear audio from the phone and speak into the phone via the headset or earbud accessory. A plug connected to the headsets, earbuds, or other peripheral device can include separate conductive elements to transfer electrical signals corresponding to the left ear audio, right ear audio, microphone audio, and ground. The plug is compatible with the mobile device audio jack. The standard headsets or earbud accessories are configured to be placed over or attached to the ear(s) of a person, and include one or more speakers and a microphone. The headset may also include an arm that is attached to a housing that supports the microphone. The arm may be movable between a stored position and an extended, operative position. The headset, earbuds, the arm, and/or other types of peripheral devices may include one or more physiological or biometric sensors, environmental sensors, and/or other types of data-producing elements.

Computing devices, communication devices, imaging devices, electronic devices, accessories, or other types of peripheral devices designed to be worn or attached to a user (denoted as wearables or wearable devices) and the associated user experience are also becoming very popular. Mobile phone headsets and earbud accessories are examples of such wearables. Because wearable devices are typically worn by or attached to the user all or most of the time, it is important that wearables serve as a helpful tool aiding the user when needed, and not become an annoying distraction when the user is trying to focus on other things.

One form of a wearable device is a heart rate (HR) monitor. Existing heart rate monitoring solutions in the market are mostly electrocardiogram (ECG) based chest straps that transmit data to a watch that has a display. An electrocardiogram (EKG or ECG) is a test that determines heart rate based on the electrical activity of the heart. Other types of conventional HR monitors are also ECG based, but only have a watch on one hand and the user needs to pause to measure HR by touching it with the other hand. A Valencell™ brand product has a PPG (photoplethysmography) based solution for HR monitoring in earphones. PPG is an optical sensing technique that allows measurement of blood pulsation from the skin surface. The Valencell™ brand product has a sensor in the earbud and a digital signal processor (DSP) and Bluetooth™ radio in a medallion or other separate component connected to the earbuds. The user can clip the separate medallion on their clothes or wear the separate component. HR data is wirelessly transmitted periodically from the medallion or other separate component to an app in a mobile phone. Other biometric data like calories, VO2 (oxygen consumption), etc. can also be calculated by the app in the mobile phone. However, for wearable devices and other peripheral devices, it is very important to be able to ascertain the user's environment and context. Although existing systems gather some forms of biometric data, this data is not used to determine a user's environment and context nor used to make decisions based on a user's dynamically determined context.

BRIEF DESCRIPTION OF THE DRAWINGS

The various embodiments are illustrated by way of example, and not by way of limitation, in the figures of the accompanying drawings in which.

DETAILED DESCRIPTION

Figure 1:
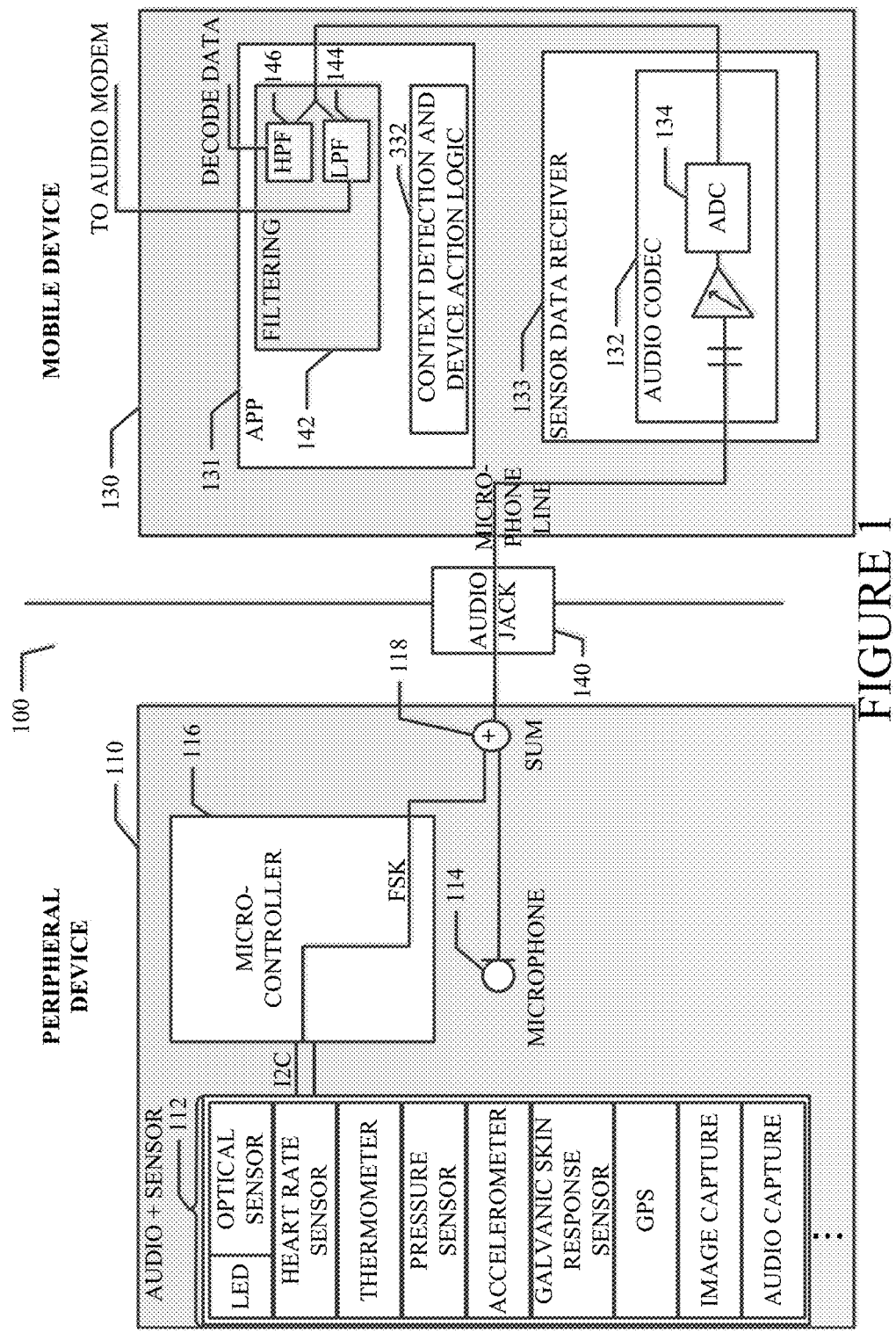
FIG. 1 illustrates an example embodiment configured for sending data from a peripheral device to a mobile device via the audio/microphone wire and the audio jack.

In the following description, for purposes of explanation, numerous specific details are set forth in order to provide a thorough understanding of the various embodiments. It will be evident, however, to one of ordinary skill in the art that the various embodiments may be practiced without these specific details.

In the various embodiments described herein, a system and method for device action and configuration based on user context detection from sensors in peripheral devices are disclosed. The various embodiments described herein provide various ways to determine status and detect events to ascertain the user's context, and to make actionable decisions based on the determined context.

In an example embodiment described herein, a peripheral device, such as a wearable device (e.g., a headset or earbuds), is configured to include a data-producing component. In one embodiment, the data-producing component can be a biometric sensor, such as a heart rate sensor, which can produce sensor data in the peripheral device. In the example embodiment, this sensor data can be transmitted to a mobile device, such as a mobile phone, with which the peripheral device is in data communications via a wired or a wireless data connection. In an embodiment using a wireless data connection, a standard wireless protocol, such as a Bluetooth™ link, or frequency modulation (FM) radio can be used. In an embodiment using a wired data connection, the peripheral device can be coupled to a mobile device via an audio/microphone wire and an audio jack of the mobile device. The sensor data can be transferred from the peripheral device to the mobile device via the microphone conductor of the audio jack. In various embodiments, the described data-producing component(s) in the peripheral device can be an accelerometer, a galvanic skin response (GSR) detector, a temperature sensor, a pressure sensor, and/or the like. It will be apparent to those of ordinary skill in the art in view of the disclosure herein that many other types of data-producing components in the peripheral device may be similarly deployed. For example, these other types of data-producing components can include environmental sensors, motion sensors, image or video-producing devices, audio capture devices, global positioning systems (GPS), and the like. Additionally, these data-producing components in the peripheral device can be grouped into sensor modules that include a variety of different types of sensors or other types of data-producing components. In each case, the data captured or generated by the data-producing components in the peripheral device can be transferred to a mobile device via a wired or wireless data connection as described. Various embodiments are described in more detail below.

In an example embodiment described herein, the data captured or generated by the data-producing components in the peripheral device (denoted sensor data) can be transferred to a software application (app) executing in the mobile device. The app can use the sensor data to detect status and events based on the dynamic conditions measured or determined by the sensors in the peripheral devices that are used regularly by people. The sensor data allows the app in a mobile device to determine the user's context (e.g., if the user is engaged in activities and does not want to be disturbed, if the user is looking for help and suggestions from the device, or the like). In other words, the sensor data received from the data-producing components in the peripheral device allow the system to determine the context of the user. From the user context, the system can also offer the help that the user is looking for more easily. Based on the dynamically determined context, the system can also automatically perform actions, suppress actions, or configure system functionality in a manner consistent with the dynamically determined context. These data-producing components in the peripheral device also allow the user and the system to monitor user wellness in real-time and over extended periods of time thereby enabling the user to make positive lifestyle changes.

The various embodiments described herein enable the system to receive sensor data from a plurality of peripheral device sensors, determine user context from the sensor data, and to make contextually-appropriate decisions for the user. In this manner, the system can be a useful tool for the user. The system can automatically determine user context based on real-time user and environmental context events and status that are detected using data from sensors installed in peripheral devices. The context events that can be dynamically determined by the system can include: what the user is doing, how the user is feeling, what kind of assistance the user needs, whether the user wants assistance or wants not be disturbed at all, how is the user's health impacted by certain activities, and a variety of other user-relevant states and/or events.

Referring now to FIG. 1, an example embodiment 100 described herein is configured for sending data from a peripheral device to a mobile device via the audio/microphone wire and the audio jack. In the embodiment of FIG. 1, a peripheral device 110 (e.g., headsets, earbuds, or the like) can include one or more sensors 112. As described above, these sensors can be biometric sensors, environmental sensors, or other data-producing components. In a particular example embodiment, the sensors can be optical sensors for detecting heart rate, an infrared (IR) LED, an accelerometer, and/or the like. The peripheral device 110 can also include a microphone 114, which can transfer audio signals from the peripheral device 110 to a mobile device 130 via an electrical (audio/microphone) wire and audio jack in a standard manner. The peripheral device 110 can also be configured to include a microcontroller (e.g., an MSP430, or other type of microcontroller). It will be apparent to those of ordinary skill in the art in view of the disclosure herein that a variety of standard microcontrollers, application specific integrated circuits (ASICs), field programmable gate arrays (FPGAs), discrete logic circuits, or other circuitry or logic can be similarly used as the microcontroller of the example embodiments. The microcontroller 116 can receive the sensor data produced by the sensors 112. The sensor data produced by the one or more sensors 112 in the peripheral device 110 can be encoded into a modulation format and sent to the microcontroller 116 for processing. In one example embodiment, the sensor data is provided as I2C signals. I2C (also denoted I$^2$C or Inter-Integrated Circuit) is a multimaster, serial, single-ended computer bus used for attaching low-speed peripherals to a motherboard, embedded system, cellphone, or other electronic device. It will be apparent to those of ordinary skill in the art that the sensor data can be provided in a variety of different forms, formats, protocols, or signals. The microcontroller 116 can convert the sensor data to an audio band signal using FSK (frequency-shift keying) or other well-known encoding technique. The converted data from the sensors 112 is added into or otherwise combined with the audio/microphone wire signals using an adder 118 for transfer to a mobile device 130 via the standard audio jack 140.

Referring still to FIG. 1, a mobile device 130 of an example embodiment is shown coupled to the peripheral device 110 via audio jack 140. It will be apparent to those of ordinary skill in the art that devices other than a mobile phone can be similarly used. For example, the mobile device 130 can also include a smartphone, a tablet device, laptop computer, a personal digital assistant (PDA), global positioning system (GPS) device, an imaging device, an audio or video player or capture device, or other form of mobile computing, communications, or imaging device. Such mobile devices 130 can include standard components, such as an audio encoder/decoder (codec) 132 and analog-to-digital converter (ADC) 124 as part of a sensor data receiver 133. As described above, mobile device 130 can also include an application (app) 131, which can comprise downloaded software, firmware, or other form of customized processing logic. App 131 can be configured to include a filtering component 142 and Context Detection and Device Action Logic 332. Filtering component 142 can include a low pass filter (LPF) 144 and a high pass filter (HPF) 146. App 131 can also be configured as processing logic or logic, at least a portion of which is partially implemented in hardware, the logic including the filtering component 142 and the Context Detection and Device Action Logic 332. The Context Detection and Device Action Logic 332 of an example embodiment is described in more detail below.

Sensor data sent from the peripheral device 110 to the mobile device 130 via the audio/microphone wire and the audio jack 140 is received at the sensor data receiver 133 and sampled in the standard codec 132 provided in a conventional mobile device 130. The codec 132 can use the analog-to-digital converter (ADC) 134, to produce digital signals that are received by the filtering component 142 of the app 131 executing on the mobile device 130. The LPF 144 can be used to isolate the standard audio signals produced by microphone 114. These audio signals can be passed to an audio modem. The HPF 146 can be used to isolate the encoded sensor data received from the sensors 112. The isolated sensor data can be passed to a decoder component, which processes and analyzes the sensor data produced in peripheral device 110. In this manner, the example embodiment can send sensor data produced in a peripheral device to a mobile device for processing by a mobile device app via the audio/microphone wire and the audio jack of the mobile device. The described embodiment provides the advantage that sensor data can be transferred from the peripheral device to the mobile device via the audio jack without having to modify the hardware of the mobile device. Further, the embodiment does not require a wireless connection to the mobile device.

Figure 2:
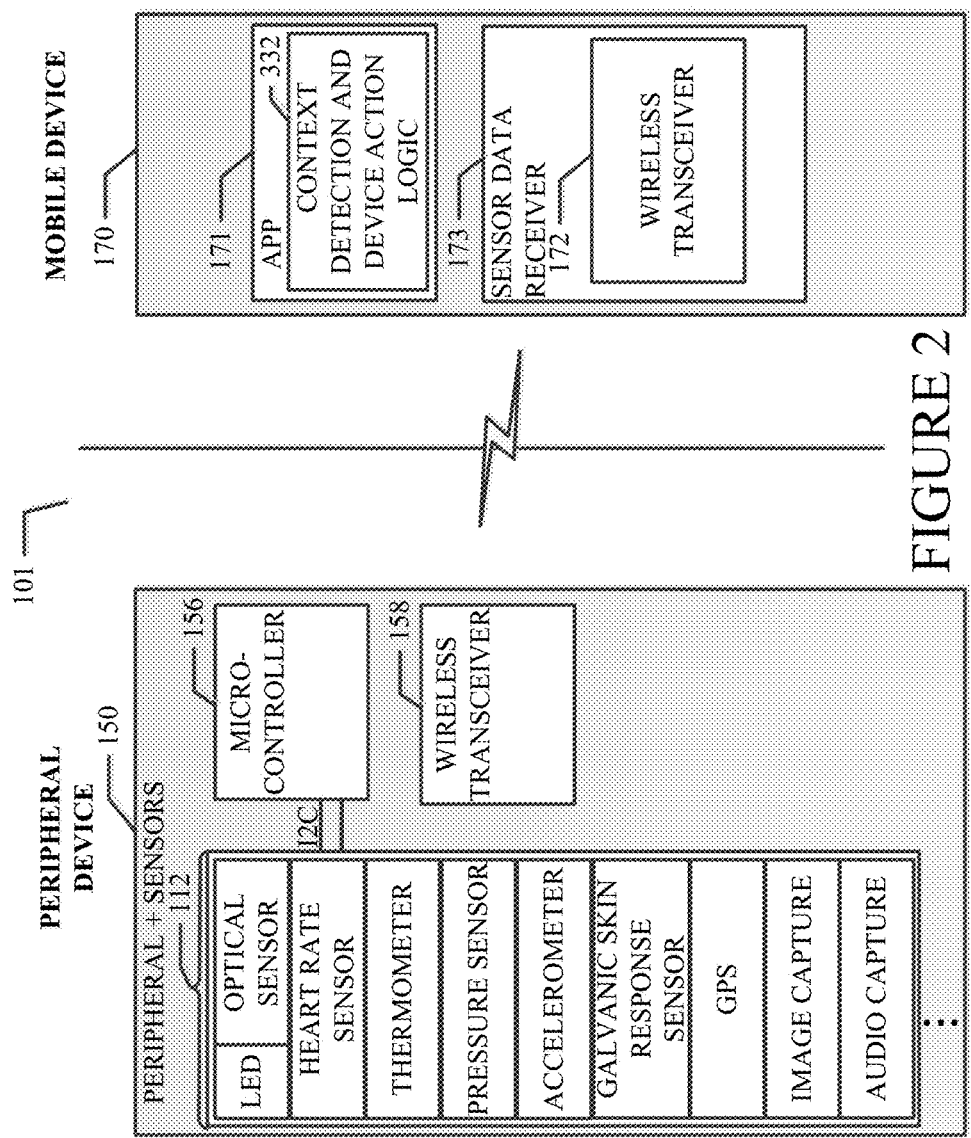
FIG. 2 illustrates an example embodiment configured for sending data from a peripheral device to a mobile device via a wireless data connection.

However, referring now to FIG. 2, in another example embodiment 101, data transfer from the peripheral device 150 to the mobile device 170 can be effected using standard Bluetooth™ Low Energy technology or frequency modulation (FM) radio signals provided by a wireless transceiver 158 in the peripheral device 150. In the example embodiment shown in FIG. 2, the peripheral device 150 (e.g., headsets, earbuds, or the like) can include one or more sensors 112. As described above, these sensors can be biometric sensors, environmental sensors, or other data-producing component. Peripheral device 150 can also be configured to include a microcontroller 156. It will be apparent to those of ordinary skill in the art in view of the disclosure herein that a variety of standard microcontrollers, application specific integrated circuits (ASIC s), field programmable gate arrays (FPGAs), discrete logic circuits, or other circuitry or logic can be similarly used as the microcontroller of the example embodiments. The microcontroller 156 can receive the sensor data produced by the sensors 112. The sensor data produced by the one or more sensors 112 in the peripheral device 150 can be encoded into a pre-defined data format by the microcontroller 156 and sent to the wireless transceiver 158. The wireless transceiver 158 allows the peripheral device 150 to wirelessly transmit peripheral device data, such as sensor data from sensors 112 to the mobile device 170. A wireless transceiver 172 of the sensor data receiver 173 in the mobile device 170 allows the mobile device 170 to receive sensor data wirelessly from the peripheral device 150. As described above, mobile device 170 can also include an application (app) 171, which can comprise downloaded software, firmware, or other form of customized processing logic. The app 171 can include Context Detection and Device Action Logic 332. The Context Detection and Device Action Logic 332 of an example embodiment is described in more detail below. The app 171 can receive the sensor data from the wireless transceiver 172 via the sensor data receiver 173. In this manner, the example embodiment can transfer sensor data produced in a peripheral device to a mobile device for processing by a mobile device app via a wireless data connection. The Bluetooth™ solution would be simpler, but would also be more costly and would consume more electrical power. The FM solution would require modifications to the mobile device and may not work with any mobile phone.

The various embodiments described herein detect a particular state or event based on sensor data received from a peripheral device, and then determine the broader user context based on the state/event detection. For example, sensor data received from a peripheral device can be used to infer the user context, which can be used to determine if the user is having a meal, or snacking, or drinking, or engaged in other identifiable activities, so the system can take actions based on the broader context. According to various example embodiments, the following usages describe examples of the system behaviors and capabilities in response to detection of certain user context events or states.

Figure 3:
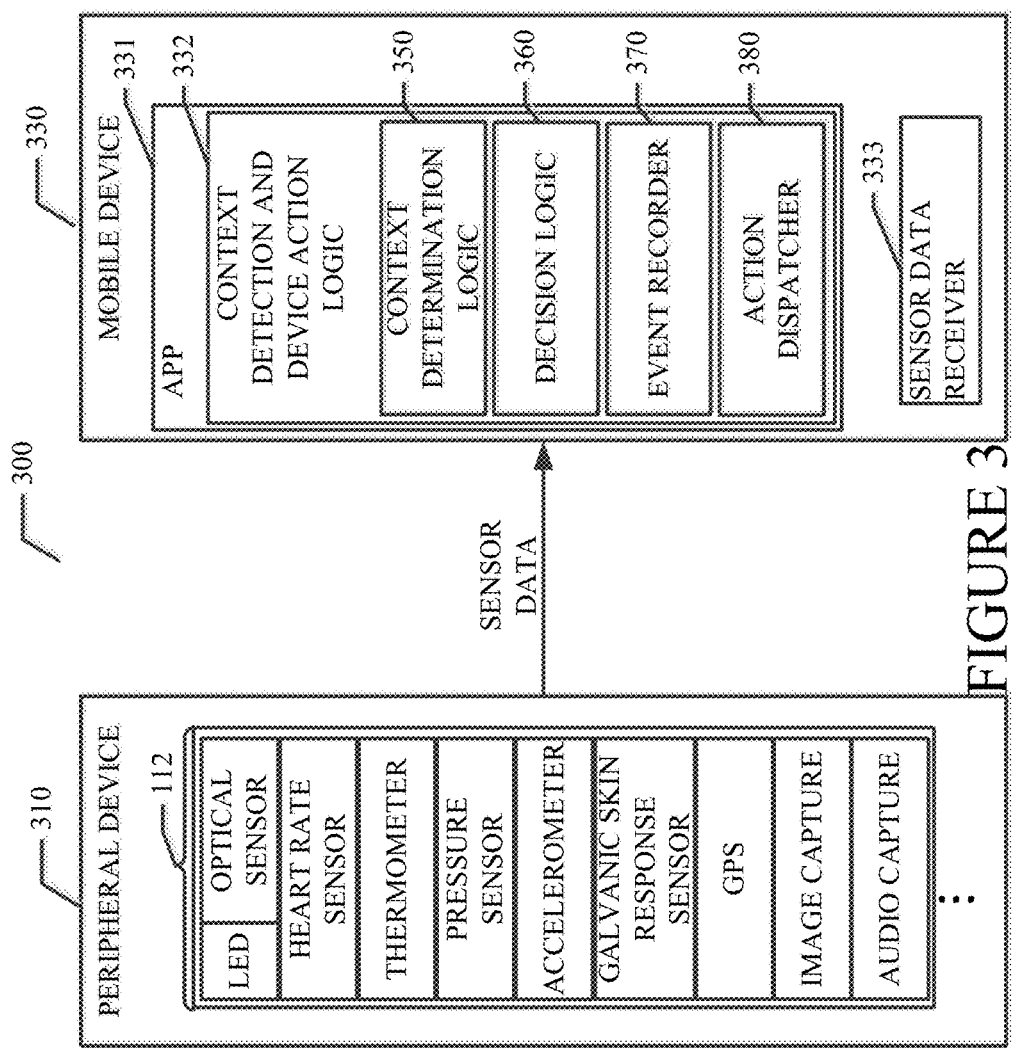
FIG. 3 illustrates a system diagram of an example embodiment.
Figure 4:
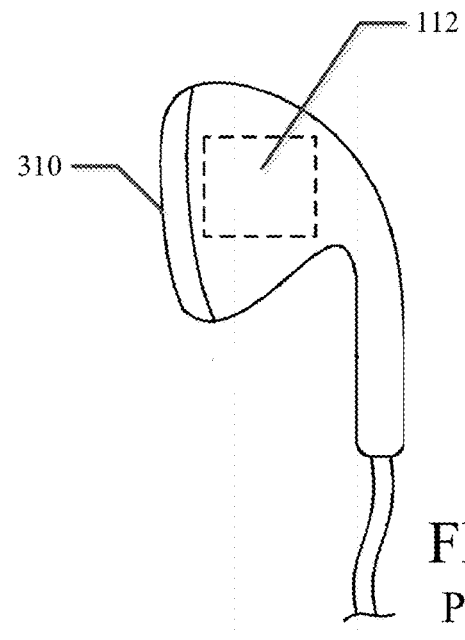
FIGS. 4 through 6 illustrate examples of the placement of sensors in various types of peripheral devices (e.g., headsets and earbuds)
Figure 5:
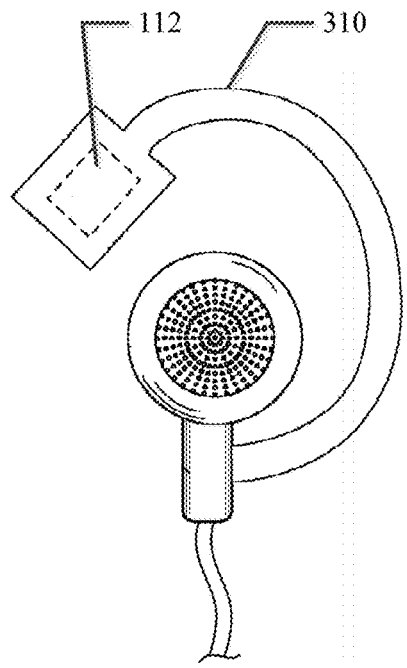
Figure 6:
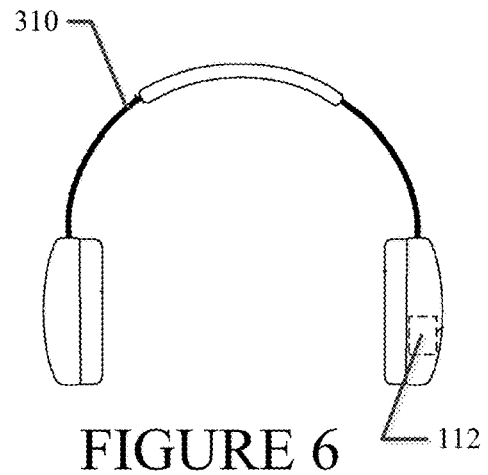

Referring now to FIG. 3, a system diagram 300 of an example embodiment is illustrated. As described above, a peripheral device 310 can include a plurality of sensors or other data-generating components 112. Examples of the placement of sensors in various types of peripheral devices (e.g. headsets and earbuds) are shown in FIGS. 4 through 6. Sensor data generated by these sensors 112 can be transferred to the mobile device 330 and received by the sensor data receiver 333 in several ways as also described above. The sensor data is processed in the mobile device 330 by Context Detection and Device Action Logic 332 executing in a processing environment provided by app 331. Logic 332 comprises a plurality of processing modules for processing the sensor data to determine a context and to perform actions based on the determined context. In particular, the Logic 332 includes Context Determination Logic 350, Decision Logic 360, an Event Recorder 370, and an Action Dispatcher 380. The data processing performed by each of these processing modules is described below in relation to several described example embodiments.

Figure 7:
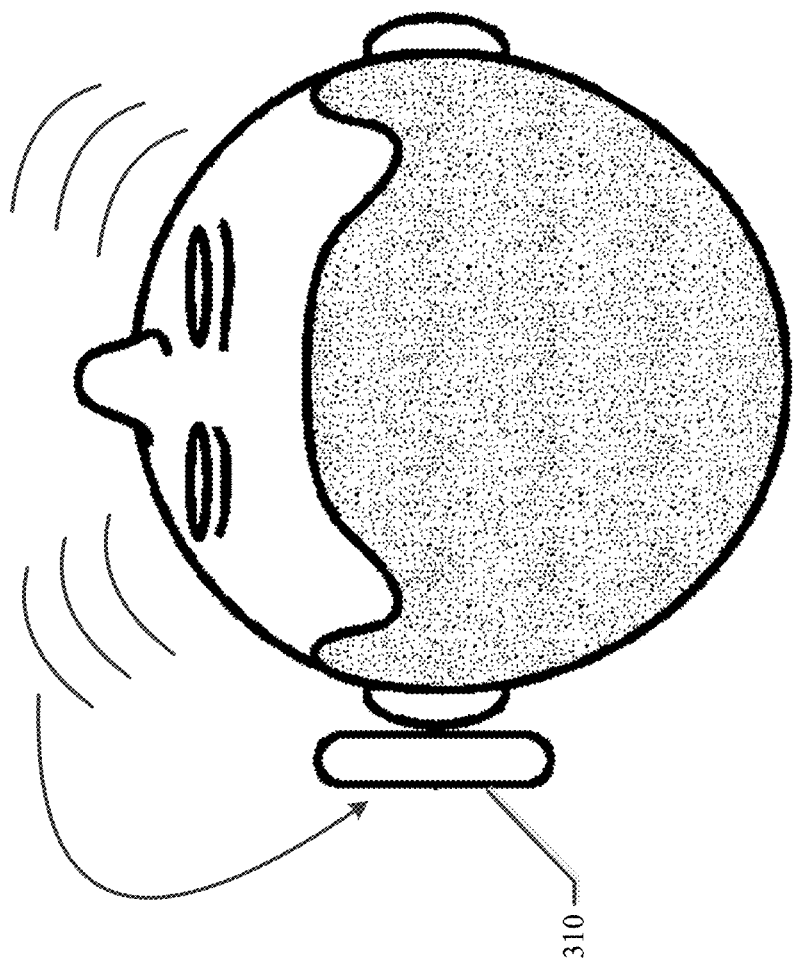
FIGS. 7 through 9 illustrate example embodiments in which accelerometer data with a microphone input can be used to detect movement and/or sounds of the user associated with chewing and a type of food being eaten.
Figure 8:
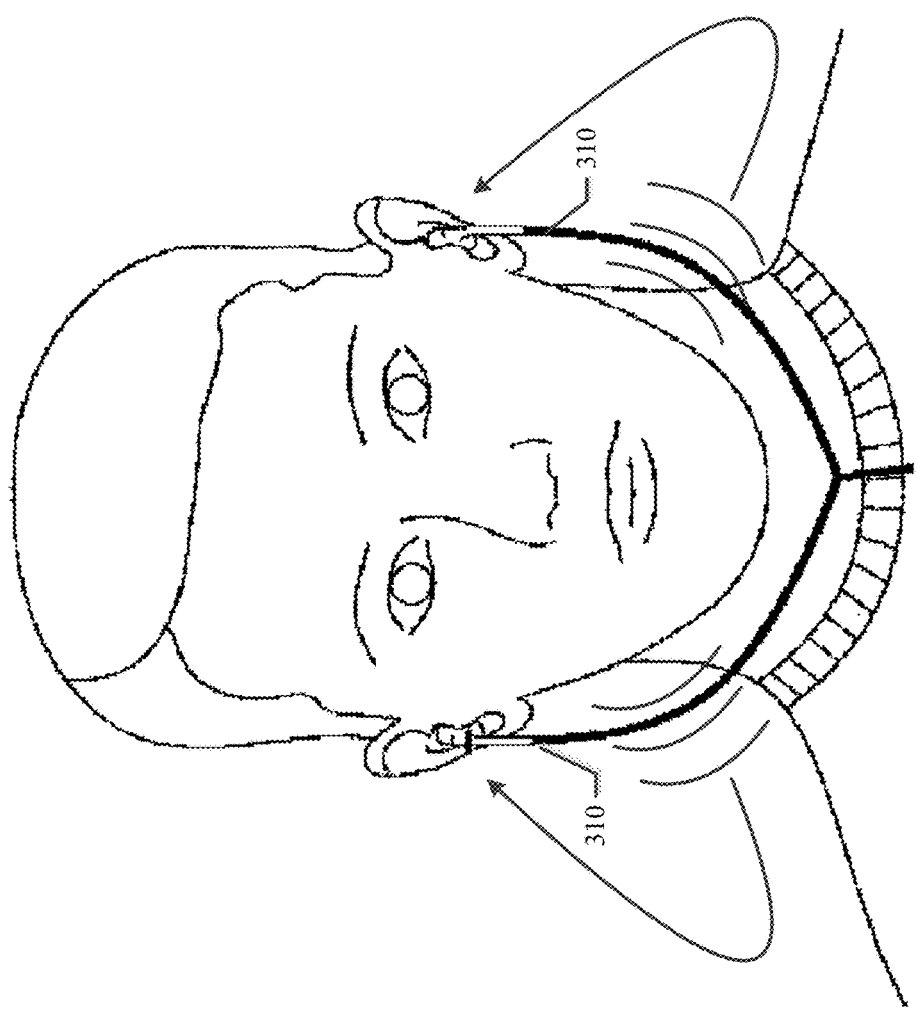
Figure 9:
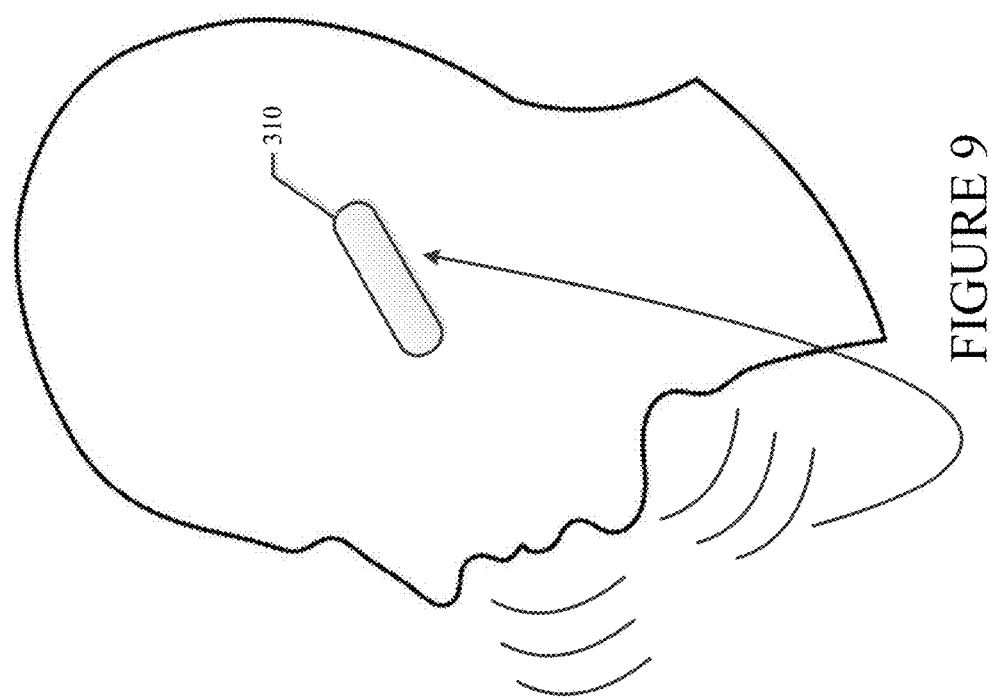

In a first example embodiment, an accelerometer and/or a microphone or other audio capture device of data-generating components 112 in the peripheral device 310 is used for detecting that a user is chewing. As shown in FIGS. 7 through 9, accelerometer data with a microphone input can be used to detect movement and/or sounds of the user associated with chewing and a type of food being eaten (e.g., crunchy, chewy, or soft food). This data can be used by the Context Determination Logic 350 to determine if the user is having a meal. In this example embodiment, the determined context is one associated with the user having a meal. This context determination is passed from the Context Determination Logic 350 to the Decision Logic 360. This context determination and any associated detected events or states can also be logged by an Event Recorder 370. The Decision Logic 360 can use the context determination to make a decision related to performing (or not performing) an action based on the determined context. For example in a particular embodiment, the Decision Logic 360 can cause the mobile device 330, via the Action Dispatcher 380, to trigger or configure one or more of the actions described below based on the determined context:

Device Action 1: If the user doesn't want to be disturbed during dinner based on a pre-configured preference, the mobile device 330 can be configured by the Action Dispatcher 380 to suppress notifications during the meal or other detected events.

Device Action 2: Because the determined context is one associated with the user having a meal, the mobile device 330 can be configured by the Action Dispatcher 380 to set a reminder that is triggered after completion of the meal. For example, the mobile device 330 can be configured to automatically remind the user to take his/her medicine after lunch.

Device Action 3: Based on the sensor data, such as the accelerometer data and/or microphone input used to detect movement and/or sounds of the user associated with chewing, the Context Determination Logic 350 can determine the rate at which the user is chewing and swallowing. If the user is determined to be swallowing too quickly based on the user's determined rate in comparison to pre-stored data corresponding to normative standards for human chewing and swallowing, the mobile device 330 can be configured by the Action Dispatcher 380 to issue a notification to the user to gently coach her/him to slow down and chew/swallow properly.

Device Action 4: Based on the sensor data and the determination that the user is eating, the Context Determination Logic 350 can also determine the times of day and lengths of time when the user is eating. If the user is determined to be eating for a short period of time, or intermittently, then the Context Determination Logic 350 can determine the user is snacking and log the activity using the Event Recorder 370. Based on the sensor data, such as the accelerometer data and/or microphone input used to detect movement and/or sounds of the user associated with chewing, the Context Determination Logic 350 can also determine the likely type of food being consumed (e.g., a crunchy, chewy, or soft food). The Context Determination Logic 350 can also be configured to prompt the user to enter information identifying the type of snack they are consuming. This log can give an accurate calorie consumption picture for the user over a pre-determined time frame.

It will be apparent to those of ordinary skill in the art in view of the disclosure herein that a variety of different actions can be triggered or configured based on the detection of a context associated with a user consuming a meal.

In a second example embodiment, a heart rate monitor or sensor and/or a GSR (galvanic skin response) sensor of data-generating components 112 in the peripheral device 310 can be used for detecting stress in the user. The heart rate of the user as detected by the heart rate sensor can be compared with pre-stored normative standards of human heart rates. Elevated heart rates can be indicative of stress. The GSR sensor measures the electrical conductance of the skin, which can be indicative of moisture or sweat on the skin. Skin moisture/sweat levels can be compared with pre-stored normative standards of human skin moisture/sweat levels. Elevated skin moisture/sweat levels can be indicative of stress. This data can be used by the Context Determination Logic 350 to determine if the user is experiencing a stress episode. The Context Determination Logic 350 can also determine the timing, length, and severity of the detected stress episode. This information can be logged using the Event Recorder 370. Additionally, the context determination (e.g., a stress episode) can be passed from the Context Determination Logic 350 to the Decision Logic 360. The Decision Logic 360 can use the context determination to make a decision related to performing (or not performing) an action based on the determined context. For example in a particular embodiment, the Decision Logic 360 can cause the mobile device 330, via the Action Dispatcher 380, to trigger or configure one or more of the actions described below based on the determined context:

Device Action 5: Upon the detection of the user stress episode, the mobile device 330 can be configured by the Action Dispatcher 380 to issue a notification or warning to the user and suggest that s/he take a break and relax. The mobile device 330 can also be configured by the Action Dispatcher 380 to issue a notification or warning to a third party (e.g., call or text paramedics) based on the timing, length, and/or severity of the detected stress episode. The mobile device 330 can also be configured by the Action Dispatcher 380 to issue a notification or warning to a third party based on the detection of the cessation of heart beat or other events associated with emergency situations or severe medical conditions.

Device Action 6: Given the detection of user stress over time, the Context Determination Logic 350 and the Decision Logic 360 can build datasets to enable the user to look at his/her cumulative stress data and determine stress patterns, such as the time of the day or the specific tasks being performed that are producing higher levels of stress in the user.

Device Action 7: Upon the detection of the user stress episode, the mobile device 330 can be configured by the Action Dispatcher 380 to suppress notifications until the stress level is reduced.

It will be apparent to those of ordinary skill in the art in view of the disclosure herein that a variety of different actions can be triggered or configured based on the detection of a context associated with a user stress episode or medical condition.

In a third example embodiment, a temperature sensor (thermometer) of data-generating components 112 in the peripheral device 310 can be used for detecting and monitoring the user's core body temperature in real-time. The user's real-time body temperature as measured by the thermometer can be compared with pre-stored normative standards of human body temperature. Elevated body temperature can be indicative of disease, infection, stress, or other medical condition. This data can be used by the Context Determination Logic 350 to determine if the user is experiencing a medical condition. The Context Determination Logic 350 can also determine the timing, length, and severity of the detected medical condition. This information can be logged using the Event Recorder 370. Additionally, the context determination (e.g., a medical condition) can be passed from the Context Determination Logic 350 to the Decision Logic 360. The Decision Logic 360 can use the context determination to make a decision related to performing (or not performing) an action based on the determined context. For example in a particular embodiment, the Decision Logic 360 can cause the mobile device 330, via the Action Dispatcher 380, to trigger or configure one or more of the actions described below based on the determined context:

Device Action 8: Upon the detection of the elevated user body temperature relative to comparisons with nominal core body temperature data, the mobile device 330 can be configured by the Action Dispatcher 380 to issue a notification or warning to the user notifying the user of the presence of slight fevers that may be signs of oncoming infection. The mobile device 330 can also be configured by the Action Dispatcher 380 to issue a notification or warning to a third party (e.g., call or text paramedics) based on the timing, length, and/or severity of the detected medical condition. The mobile device 330 can also be configured by the Action Dispatcher 380 to issue a notification or warning to a third party based on the detection of the user's core body temperature being above or below a safe level or other events associated with emergency situations or severe medical conditions.

It will be apparent to those of ordinary skill in the art in view of the disclosure herein that a variety of different actions can be triggered or configured based on the detection of a context associated with a user medical condition.

In a fourth example embodiment, a heart rate monitor or sensor of data-generating components 112 in the peripheral device 310 can be used for detecting the user's mood. The heart rate of the user as detected by the heart rate sensor can be compared with pre-stored normative standards of human heart rates associated with particular moods. Elevated heart rates can be indicative of energetic or active moods. Slower heart rates can be indicative of more mellow or somber moods. This data can be used by the Context Determination Logic 350 to determine the user's mood. The Context Determination Logic 350 can also determine the timing, length, and severity of the detected mood. This information can be logged using the Event Recorder 370. Additionally, the context determination (e.g., the user's mood) can be passed from the Context Determination Logic 350 to the Decision Logic 360. The Decision Logic 360 can use the context determination to make a decision related to performing (or not performing) an action based on the determined context. For example in a particular embodiment, the Decision Logic 360 can cause the mobile device 330, via the Action Dispatcher 380, to trigger or configure one or more of the actions described below based on the determined context:

Device Action 9: Upon the detection of the user's mood, the mobile device 330 can be configured by the Action Dispatcher 380 to play only relevant sections of a song to maintain the user's heart rate. Software in the app 331 running in the mobile device 330 can analyze a song and determine the song's BPM (beats per minute) at different sections of the song. Different songs or various portions of a song can be matched to the current heart rate of the user as measured by the heart rate monitor in the peripheral device 310. For example, if the user's heart rate, and thus the user's mood, is suggestive of music with a pace of 180 BPM, the app 331 can play only the part of a song where the song's BPM is 180, instead of playing the complete song. If the target pace is 180 BPM and the current song has ended, the next song can be played 30 seconds, for example, from its start to avoid a low tempo beginning, so the user doesn't slow down and the target pace is maintained. In this manner, the embodiment can match multimedia content with the current mood of the consumer.

It will be apparent to those of ordinary skill in the art in view of the disclosure herein that a variety of different actions can be triggered or configured based on the detection of a context associated with a user's mood.

In other various embodiments, the sensors of data-generating components 112 in the peripheral device 310 can be used for detecting other user contexts. For example, the pressure sensor can be used to measure atmospheric pressure and thereby infer certain weather conditions. A user can be notified of rapid changes in pressure, which may be indicative of the approach of weather events. In other embodiments, a global positioning system (GPS) receiver of the data-generating components 112 can be used to determine the location of the user. For example, the Context Determination Logic 350 can use GPS data to determine if a user is currently at work or at a residence. The mobile device 330 can be configured differently depending on the location of the user. The GPS data can also be used to determine if the user is stationary or moving. In other embodiments, image or audio capture devices of the data-generating components 112 can be used to record audio or video clips in the proximity of the user. Static images can also be taken. The recordings can transferred to the app 331 where they can be parsed and analyzed to extract context information related to the user's current situation. For example, the audio and image information can be used to determine that the user is walking in the city based on traffic noise or images corresponding to city locations.

It will be apparent to those of ordinary skill in the art in view of the disclosure herein that a variety of other well-known sensing devices or technologies can be included in the sensor modules added to the peripheral device 310. As such, it will be apparent to those of ordinary skill in the art in view of the disclosure herein that a variety of additional user-associated states and events can be detected and contextually relevant actions can be taken (or suppressed) in response thereto.

Figure 10:
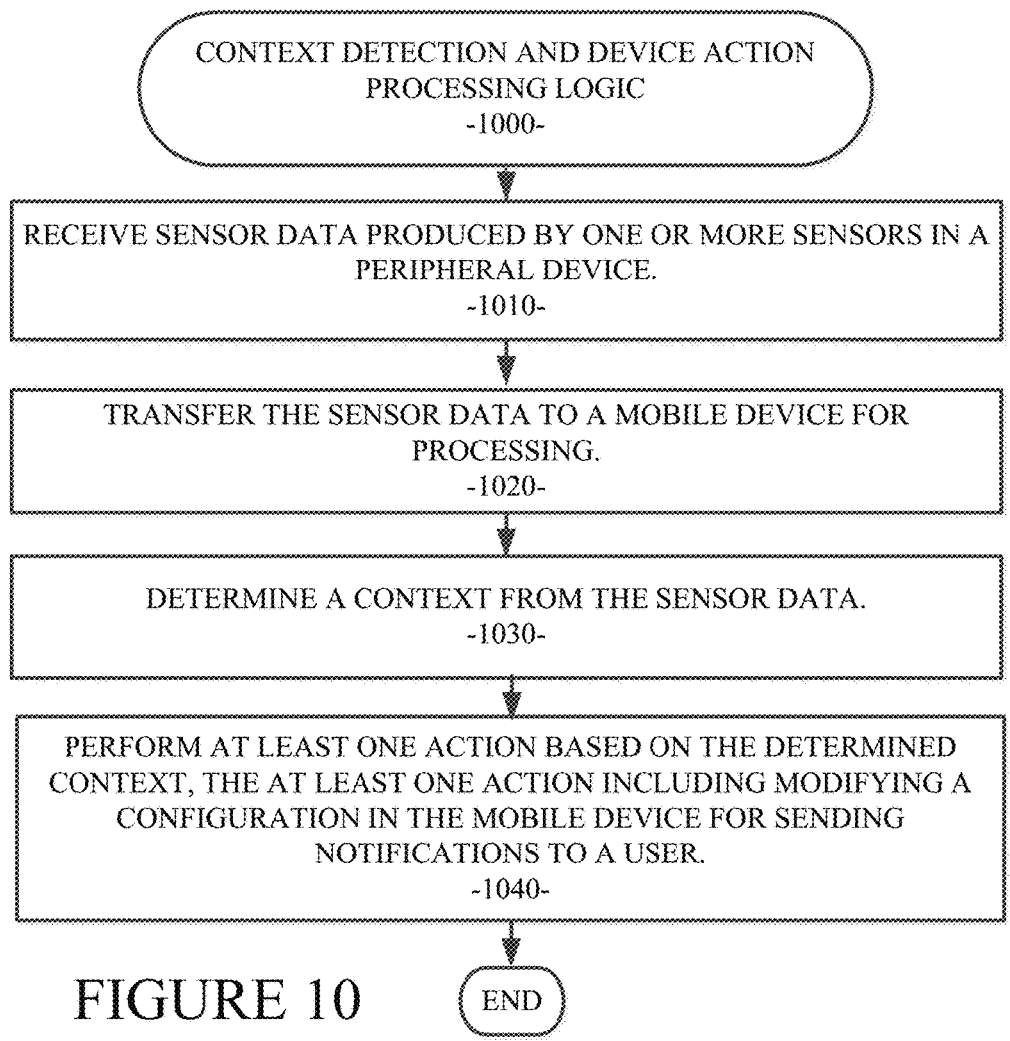
FIG. 10 is a processing flow chart illustrating an example embodiment of a method as described herein.

Referring now to FIG. 10, a processing flow diagram illustrates an example embodiment of a method for device action and configuration based on user context detection from sensors in peripheral devices as described herein. The method 1000 of an example embodiment includes: receiving sensor data produced by one or more sensors in a peripheral device (processing block 1010); transferring the sensor data to a mobile device for processing (processing block 1020); determining a context from the sensor data (processing block 1030); and performing at least one action based on the determined context, the at least one action including modifying a configuration in the mobile device for sending notifications to a user (processing block 1040).

Figure 11:
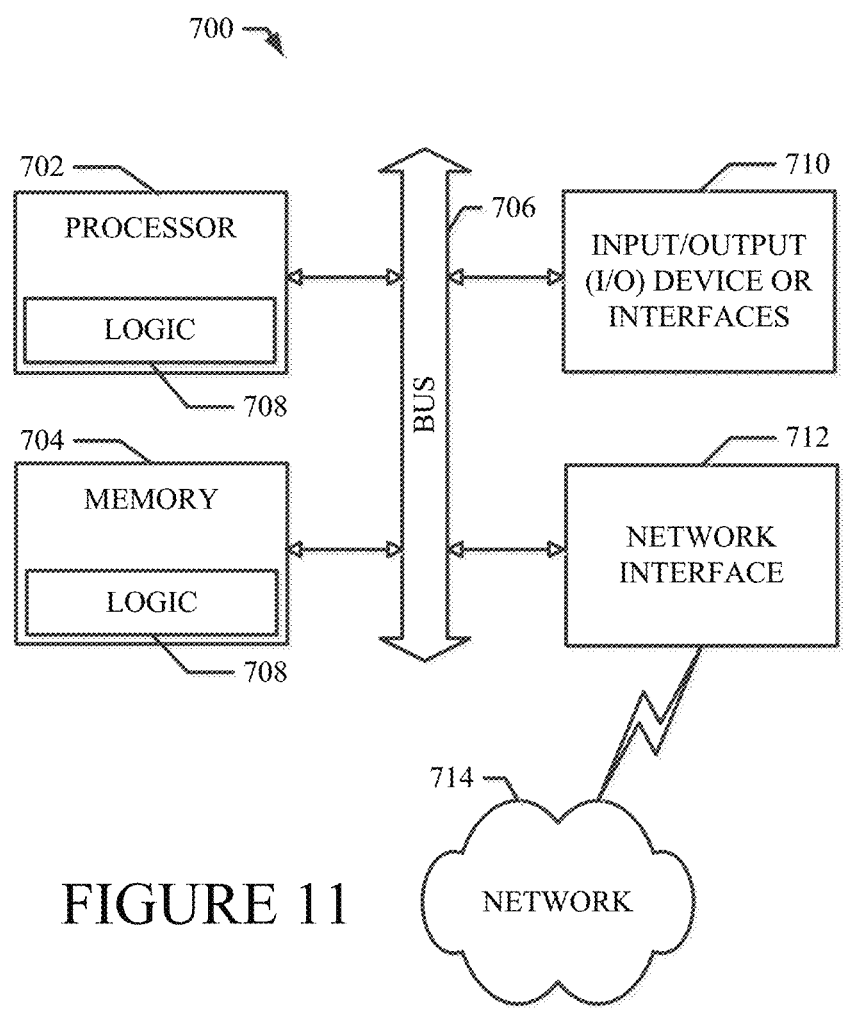
FIG. 11 shows a diagrammatic representation of a machine in the example form of a mobile computing and/or communication system within which a set of instructions when executed and/or processing logic when activated may cause the machine to perform any one or more of the methodologies described and/or claimed herein.

FIG. 11 shows a diagrammatic representation of a machine in the example form of a mobile computing and/or communication system 700 within which a set of instructions when executed and/or processing logic when activated may cause the machine to perform any one or more of the methodologies described and/or claimed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a laptop computer, a tablet computing system, a Personal Digital Assistant (PDA), a cellular telephone, a smartphone, a web appliance, a set-top box (STB), a network router, switch or bridge, or any machine capable of executing a set of instructions (sequential or otherwise) or activating processing logic that specify actions to be taken by that machine. Further, while only a single machine is illustrated, the term "machine" can also be taken to include any collection of machines that individually or jointly execute a set (or multiple sets) of instructions or processing logic to perform any one or more of the methodologies described and/or claimed herein.

The example mobile computing and/or communication system 700 includes a data processor 702 (e.g., a System-on-a-Chip (SoC), general processing core, graphics core, and optionally other processing logic) and a memory 704, which can communicate with each other via a bus or other data transfer system 706. The mobile computing and/or communication system 700 may further include various input/output (I/O) devices and/or interfaces 710, such as a touchscreen display, an audio jack, and optionally a network interface 712. In an example embodiment, the network interface 712 can include one or more radio transceivers configured for compatibility with any one or more standard wireless and/or cellular protocols or access technologies (e.g., 2nd (2G), 2.5, 3rd (3G), 4th (4G) generation, and future generation radio access for cellular systems, Global System for Mobile communication (GSM), General Packet Radio Services (GPRS), Enhanced Data GSM Environment (EDGE), Wideband Code Division Multiple Access (WCDMA), LTE, CDMA2000, WLAN, Wireless Router (WR) mesh, and the like). Network interface 712 may also be configured for use with various other wired and/or wireless communication protocols, including TCP/IP, UDP, SIP, SMS, RTP, WAP, CDMA, TDMA, UMTS, UWB, WiFi, WiMax, Bluetooth, IEEE 802.11x, and the like. In essence, network interface 712 may include or support virtually any wired and/or wireless communication mechanisms by which information may travel between the mobile computing and/or communication system 700 and another computing or communication system via network 714.

The memory 704 can represent a machine-readable medium on which is stored one or more sets of instructions, software, firmware, or other processing logic (e.g., logic 708) embodying any one or more of the methodologies or functions described and/or claimed herein. The logic 708, or a portion thereof, may also reside, completely or at least partially within the processor 702 during execution thereof by the mobile computing and/or communication system 700. As such, the memory 704 and the processor 702 may also constitute machine-readable media. The logic 708, or a portion thereof, may also be configured as processing logic or logic, at least a portion of which is partially implemented in hardware. The logic 708, or a portion thereof, may further be transmitted or received over a network 714 via the network interface 712. While the machine-readable medium of an example embodiment can be a single medium, the term "machine-readable medium" should be taken to include a single non-transitory medium or multiple non-transitory media (e.g., a centralized or distributed database, and/or associated caches and computing systems) that store the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

In various embodiments as described herein, example embodiments include at least the following examples.

A mobile device comprising: logic, at least a portion of which is partially implemented in hardware, the logic configured to determine a context from sensor data and to perform at least one action based on the determined context, the at least one action including modifying a configuration in a mobile device for sending notifications to a user.

The mobile device as claimed above wherein the sensor data being encoded with audio signals and received on a microphone line via a microphone conductor of an audio jack.

The mobile device as claimed above including a sensor data receiver to receive sensor data produced by one or more sensors in a peripheral device and to provide the received sensor data to the logic for processing.

The mobile device as claimed above wherein the sensor data receiver includes a wireless transceiver, the sensor data being received via a wireless data transmission.

The mobile device as claimed above wherein the sensor data is of a type from the group consisting of: biometric data, heart rate data, temperature data, pressure data, acceleration data, galvanic skin response data, and global positioning system data.

The mobile device as claimed above wherein the mobile device is a mobile phone.

A system comprising: a peripheral device including one or more sensors to produce sensor data; and logic, at least a portion of which is partially implemented in hardware, the logic configured to determine a context from the sensor data and to perform at least one action based on the determined context, the at least one action including modifying a configuration in a mobile device for sending notifications to a user.

The system as claimed above wherein the sensor data being encoded with audio signals and received on a microphone line via a microphone conductor of an audio jack.

The system as claimed above wherein the peripheral device including a microcontroller coupled to the one or more sensors to receive the sensor data generated by the one or more sensors, the microcontroller being further configured to encode the sensor data into an audio band signal, the peripheral device including an adder to combine the encoded data with audio signals on the microphone line, the adder being further configured to transfer the combined audio signals via the microphone conductor of the audio jack.

The system as claimed above including a sensor data receiver to receive the sensor data produced by the one or more sensors in the peripheral device and to provide the received sensor data to the logic for processing.

The system as claimed above wherein the peripheral device includes a wireless transceiver, the sensor data being sent via a wireless data transmission.

The system as claimed above wherein the sensor data produced by the one or more sensors in the peripheral device is biometric data.

The system as claimed above wherein the sensor data is of a type from the group consisting of: heart rate data, temperature data, pressure data, acceleration data, galvanic skin response data, and global positioning system data.

The system as claimed above wherein the logic is implemented in a mobile phone.

The system as claimed above wherein the peripheral device is from the group consisting of: a headset and an earbud accessory.

A non-transitory machine-useable storage medium embodying instructions which, when executed by a machine, cause the machine to: receive sensor data produced by one or more sensors in a peripheral device; transfer the sensor data to a mobile device for processing; determine a context from the sensor data; and perform at least one action based on the determined context, the at least one action including modifying a configuration in the mobile device for sending notifications to a user.

The machine-useable storage medium as claimed above wherein the instructions being further configured to receive the sensor data on a microphone line via a microphone conductor of an audio jack.

The machine-useable storage medium as claimed above wherein the instructions being further configured to receive the sensor data via a wireless data transmission.

The machine-useable storage medium as claimed above wherein the sensor data produced by the one or more sensors in the peripheral device is biometric data.

The machine-useable storage medium as claimed above wherein the sensor data is of a type from the group consisting of: heart rate data, temperature data, pressure data, acceleration data, galvanic skin response data, and global positioning system data.

A method comprising: determining a context from sensor data; and performing at least one action based on the determined context, the at least one action including modifying a configuration in a mobile device for sending notifications to a user.

The method as claimed above wherein the sensor data being encoded with audio signals and received on a microphone line via a microphone conductor of an audio jack.

The method as claimed above including receiving sensor data produced by one or more sensors in a peripheral device and providing the received sensor data to logic for processing.

The method as claimed above wherein the sensor data being received via a wireless data transmission.

The method as claimed above wherein the sensor data is of a type from the group consisting of: biometric data, heart rate data, temperature data, pressure data, acceleration data, galvanic skin response data, and global positioning system data.

The method as claimed above wherein the mobile device is a mobile phone.

A mobile apparatus comprising: logic means, at least a portion of which is partially implemented in hardware, the logic means configured to determine a context from sensor data and to perform at least one action based on the determined context, the at least one action including modifying a configuration in a mobile device for sending notifications to a user.

The mobile apparatus as claimed above wherein the sensor data being encoded with audio signals and received on a microphone line via a microphone conductor of an audio jack.

The mobile apparatus as claimed above including a sensor data receiving means to receive sensor data produced by one or more sensors in a peripheral device and to provide the received sensor data to the logic means for processing.

The mobile apparatus as claimed above wherein the sensor data receiving means includes a wireless transceiver, the sensor data being received via a wireless data transmission.

The mobile apparatus as claimed above wherein the sensor data is of a type from the group consisting of: biometric data, heart rate data, temperature data, pressure data, acceleration data, galvanic skin response data, and global positioning system data.

The mobile apparatus as claimed above wherein the mobile device is a mobile phone.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A mobile device comprising:
   an interface to receive audio data from a sensor of a wearable peripheral device worn by a user; and
   at least one processor to:
      identify when the user is eating based on the audio data indicating the user is at least one of chewing or swallowing, the audio data generated in response to at least one of movement or sound of the user,
      detect completion of the eating based on the audio data, and
      configure the mobile device to generate a reminder to the user in response to the detection of the completion of the eating, the reminder to remind the user to take medication following the completion of the eating.

2. The mobile device as defined in claim 1, wherein the at least one processor is structured to configure the mobile device to generate a notification to the user during the eating based on a detected rate of the at least one of the chewing or the swallowing.

3. The mobile device as defined in claim 1, wherein the at least one processor is structured to determine a type of food the user is eating.

4. The mobile device as defined in claim 3, wherein the at least one processor is structured to determine the type of food based on the audio data.

5. The mobile device as defined in claim 3, wherein the at least one processor is structured to determine the type of food based on a user response to a prompt generated at the mobile device in response to detecting that the user is eating.

6. The mobile device as defined in claim 1, wherein the at least one processor is structured to configure the mobile device to suppress additional notifications received at the mobile device during the eating.

7. The mobile device as defined in claim 1, further including an audio jack, the wearable peripheral device corresponding to one of a headset or earbuds, the wearable peripheral device in communication with the mobile device via the audio jack.

8. A hardware memory comprising instructions that, when executed, cause a mobile device to at least:
   identify when a user wearing a wearable peripheral device is eating, the eating identified based on audio data from the wearable peripheral device indicating the user is at least one of chewing or swallowing, the audio data generated in response to at least one of movement or sound of the user;
   detect termination of the eating based on the audio data; and generate a reminder to the user in response to the termination of the eating, the reminder to remind the user to take medication following the termination of the eating.

9. A method, comprising identifying, by executing an instruction with at least one processor, an ending of eating by a user wearing a wearable peripheral device, the ending of the eating identified based on audio data from a sensor of the wearable peripheral device, the audio data indicating the user is at least one of chewing or swallowing, the audio data based on at least one of movement or sound of the user; and generating, by executing an instruction with the at least one processor, a prompt to the user in response to the ending of the eating, the prompt to remind the user to take medication following the ending of the eating.

\* \* \* \* \*